United States Patent
Brinkman et al.

(10) Patent No.: US 10,310,248 B2
(45) Date of Patent: Jun. 4, 2019

(54) MICROSCOPE INCLUDING A MEDIUM CONTAINER CONTAINING AN IMMERSION MEDIUM IN WHICH A SPECIMEN CONTAINER CONTAINING AN IMMERSION MEDIUM AND A SAMPLE IS IMMERSED

(71) Applicant: OLYMPUS CORPORATION, Hachioji-shi, Tokyo (JP)

(72) Inventors: Brendan Brinkman, Hopkinton, MA (US); Yoshihiro Shimada, Kanagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/678,854

(22) Filed: Aug. 16, 2017

(65) Prior Publication Data

US 2018/0052314 A1 Feb. 22, 2018

(30) Foreign Application Priority Data

Aug. 18, 2016 (JP) .................................. 2016-160454
Feb. 16, 2017 (JP) .................................. 2017-026640

(51) Int. Cl.
*G02B 23/00* (2006.01)
*G02B 21/33* (2006.01)
(Continued)

(52) U.S. Cl.
CPC ......... *G02B 21/33* (2013.01); *G01N 21/0303* (2013.01); *G01N 21/6458* (2013.01);
(Continued)

(58) Field of Classification Search
CPC .. G02B 21/00; G02B 21/0004; G02B 21/002; G02B 21/0024; G02B 21/0032;
(Continued)

(56) References Cited

U.S. PATENT DOCUMENTS 7,751,041 B2 *  7/2010  Haga .................... G01N 21/648
                                                          356/317
9,816,916 B2 * 11/2017  Pampaloni ............. G02B 21/16
(Continued)

FOREIGN PATENT DOCUMENTS

EP        2023127 A1    2/2009
EP        3125014 A1    2/2017
(Continued)

OTHER PUBLICATIONS

Extended European Search Report (EESR) dated Feb. 9, 2018 issued in counterpart European Application No. 17186629.6.

*Primary Examiner* — Arnel C Lavarias
(74) *Attorney, Agent, or Firm* — Holtz, Holtz & Volek PC

(57) ABSTRACT

Provided is a microscope including: a chamber storing a solution in which a cuvette accommodating a solution together with a sample is immersed and that has an index of refraction identical to that of the solution; an immersion objective lens being placed outside the chamber and collecting light from the sample; a camera acquiring an image of the light collected by the lens; a targeting section moving the lens in a direction along a detection light axis thereof; and a movable stage supporting the cuvette in the chamber so as to be movable in at least a direction along the detection light axis. Each of the cuvette and the chamber has a transparent section that can transmit light coming from the sample. The lens is placed so as to face the transparent section of the cuvette with the transparent section of the chamber interposed therebetween.

20 Claims, 11 Drawing Sheets

(51) Int. Cl.
    *G01N 21/03*     (2006.01)
    *G01N 21/64*     (2006.01)
    *G02B 21/08*     (2006.01)
    *G02B 21/16*     (2006.01)
    *G02B 21/22*     (2006.01)
    *G02B 21/26*     (2006.01)
    *G02B 21/34*     (2006.01)
    *G02B 21/36*     (2006.01)
    *G02B 21/00*     (2006.01)

(52) U.S. Cl.
    CPC ....... *G02B 21/006* (2013.01); *G02B 21/0088* (2013.01); *G02B 21/086* (2013.01); *G02B 21/16* (2013.01); *G02B 21/22* (2013.01); *G02B 21/26* (2013.01); *G02B 21/34* (2013.01); *G02B 21/361* (2013.01); *G01N 2021/0342* (2013.01); *G01N 2021/0367* (2013.01)

(58) Field of Classification Search
    CPC .............. G02B 21/0052; G02B 21/006; G02B 21/0076; G02B 21/02; G02B 21/06; G02B 21/08; G02B 21/082; G02B 21/16; G02B 21/24; G02B 21/248; G02B 21/26; G02B 21/33; G02B 21/34; G02B 21/36; G02B 21/361

USPC ....... 359/362, 363, 368, 369, 385, 388, 390, 359/391, 392, 393, 396, 398
See application file for complete search history.

(56) References Cited

U.S. PATENT DOCUMENTS

| | | |
|---|---|---|
| 2004/0263961 A1 | 12/2004 | Hummel |
| 2009/0086314 A1 | 4/2009 | Namba et al. |
| 2016/0109357 A1* | 4/2016 | Lorbeer ................. G02B 21/34 250/576 |
| 2016/0153892 A1* | 6/2016 | Knebel ............. G02B 21/0032 359/385 |
| 2017/0031150 A1 | 2/2017 | Brinkman |
| 2017/0299853 A1* | 10/2017 | Ritter ................... G02B 21/367 |
| 2018/0164569 A1* | 6/2018 | Brinkman ............. G02B 21/36 |
| 2018/0196247 A1* | 7/2018 | Hufnagel ........... G02B 21/0076 |
| 2018/0224648 A1* | 8/2018 | Shimada ............ G02B 21/0032 |

FOREIGN PATENT DOCUMENTS

| | | |
|---|---|---|
| JP | 4443832 B2 | 3/2010 |
| JP | 2017032758 A | 2/2017 |
| WO | 2015184124 A1 | 12/2015 |

\* cited by examiner

MICROSCOPE INCLUDING A MEDIUM CONTAINER CONTAINING AN IMMERSION MEDIUM IN WHICH A SPECIMEN CONTAINER CONTAINING AN IMMERSION MEDIUM AND A SAMPLE IS IMMERSED

CROSS-REFERENCE TO RELATED APPLICATIONS

This application claims the benefit of Japanese Patent Applications No. 2016-160454 and No. 2017-026640, the content of which is incorporated herein by reference.

TECHNICAL FIELD

The present invention relates to a microscope.

BACKGROUND ART

There is a known microscope in which light is caused to enter a specimen along a direction intersecting the detection light axis of a detection optical system, and a three-dimensional stereoscopic image of the specimen is acquired on the basis of fluorescence that comes from the specimen and that is detected by the detection optical system (refer to, for example, Patent Literature 1 and Patent Literature 2 below). Because no regions other than the image acquisition plane are irradiated with light in these microscopes described in Patent Literature 1 and Patent Literature 2, it is possible to acquire a superior three-dimensional stereoscopic image by suppressing fluorescence fading.

Today, this technique is gaining attention not only as a technique for the purpose of obtaining a stereoscopic image of a living organism, such as zebrafish, in which target molecules are labeled with fluorescent proteins, but also as a technique that is applied to so-called drug development screening, in which pharmaceutical efficacy is evaluated by using an image analysis technique by obtaining a three-dimensional stereoscopic image of three-dimensional cultured cells, such as spheroids or organoids (artificial organ or a portion thereof), thus raising expectations for use in a wide range of applications. In addition, with this observation method there is a demand for more microscopic, higher-resolution observation in response to the desire of researchers to perform observation at resolutions with which individual cells are recognizable.

An immersion objective lens is used with this observation method in the microscopes described in Patent Literatures 1 and 2. With the microscope described in Patent Literature 1, however, when an observation position is changed by moving the container relative to the objective lens, the amount of the liquid immersion medium reserved between the objective lens and the container is reduced, and hence the liquid immersion medium needs to be replenished. In particular, this causes an inconvenience in that the longer the relative moving distance between the objective lens and the container, such as in cases where the container is composed of a plurality of arrays, the more frequently the liquid immersion medium needs to be replenished, requiring a large amount of liquid immersion medium to be prepared. There is another inconvenience in that because replenishment takes a long time, the total observation time becomes longer as replenishment becomes more frequent.

On the other hand, in the microscope described in Patent Literature 2, a sample is accommodated in a cuvette filled with a liquid immersion medium, such as a transparent solution, and, this cuvette is further accommodated in a chamber filled with liquid immersion medium and placed on an XYZ stage. In addition, the leading end section of the objective lens used for observation is immersed in the liquid immersion medium in the chamber via an anti-leak sealing member. According to the structure of the microscope in Patent Literature 2, the amount of liquid immersion medium is not reduced even when the XYZ stage is moved, and hence the above-described inconvenience with the microscope described in Patent Literature 1 can be solved.

CITATION LIST

Patent Literature

{PTL 1}
  Publication of Japanese Patent No. 4443832
{PTL 2}
  PCT International Publication No. WO 2015/184124

SUMMARY OF INVENTION

One aspect of the present invention is a microscope including: a medium container that stores a second liquid immersion medium in which a specimen container accommodating a first liquid immersion medium together with a specimen is immersed and that has an index of refraction identical to that of the first liquid immersion medium; an objective lens that is placed outside the medium container and that collects light emitted from the specimen; an image-capturing unit that acquires an image of the light collected by the objective lens; a targeting section that moves a focal position of the objective lens in a direction along a detection light axis thereof; and a movable stage that supports the specimen container in the medium container such that the specimen container can move at least in a direction along the detection light axis, wherein each of the specimen container and the medium container has a light-transmitting section capable of transmitting the light from the specimen, and the objective lens is disposed so as to face the light-transmitting section of the specimen container, with the light-transmitting section of the medium container interposed therebetween.

DESCRIPTION OF EMBODIMENTS

First Embodiment

A microscope according to a first embodiment of the present invention will now be described with reference to the drawings.

Figure 1:
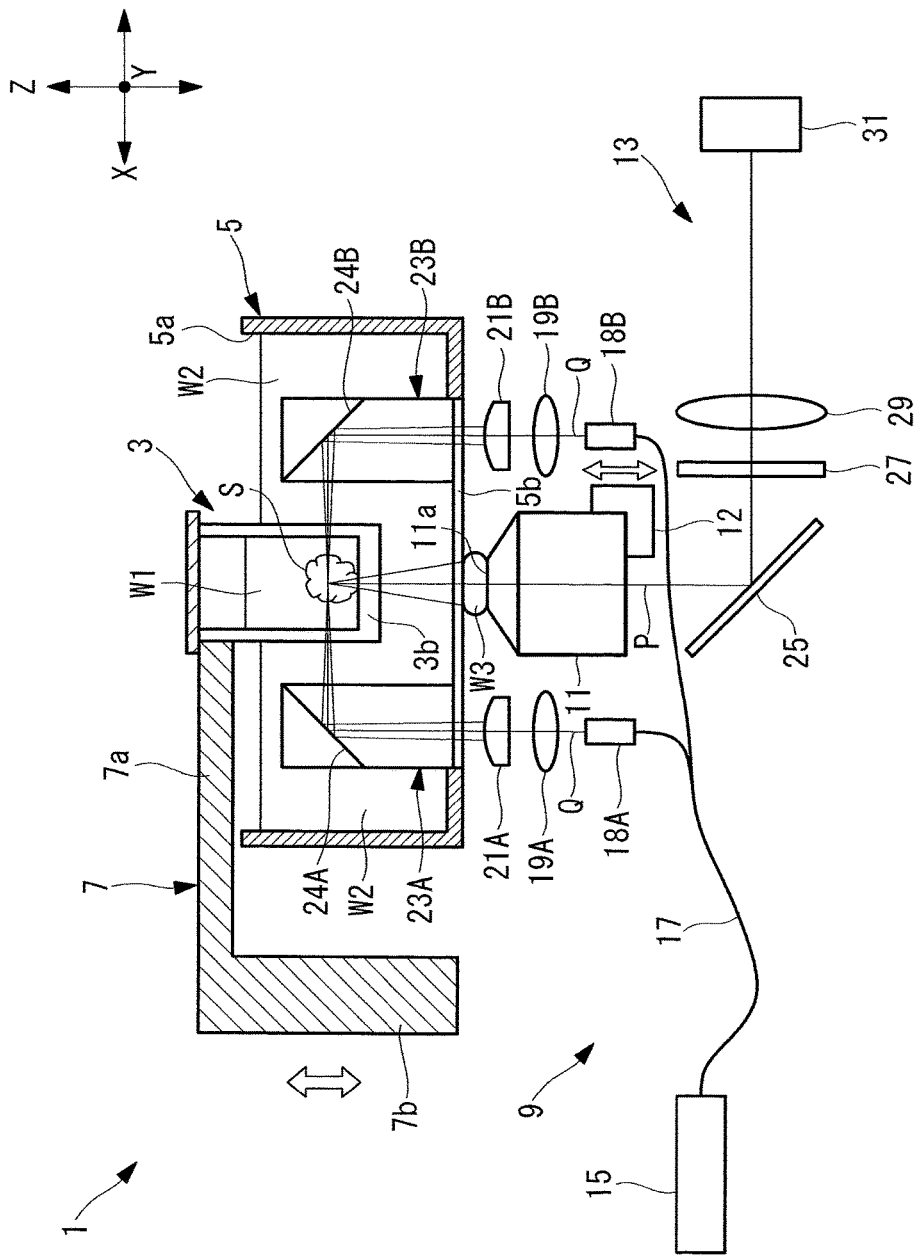
FIG. 1 is a schematic configuration diagram showing a microscope according to a first embodiment of the present invention.

As shown in FIG. 1, a microscope 1 according to this embodiment includes: a cuvette (specimen container) 3 for accommodating samples (specimens) S; a chamber (medium container) 5 that can accommodate the cuvette 3; a movable stage 7 for supporting the cuvette 3; an illumination optical system 9 for irradiating the samples S with a laser beam (light); an immersion objective lens (objective lens) 11 for collecting fluorescence emitted from the samples S; a targeting section 12 that can move the immersion objective lens 11 in a direction along a detection light axis P thereof; and an imaging optical system 13 for acquiring an image of the samples S on the basis of the fluorescence collected by the immersion objective lens 11.

Figure 2:
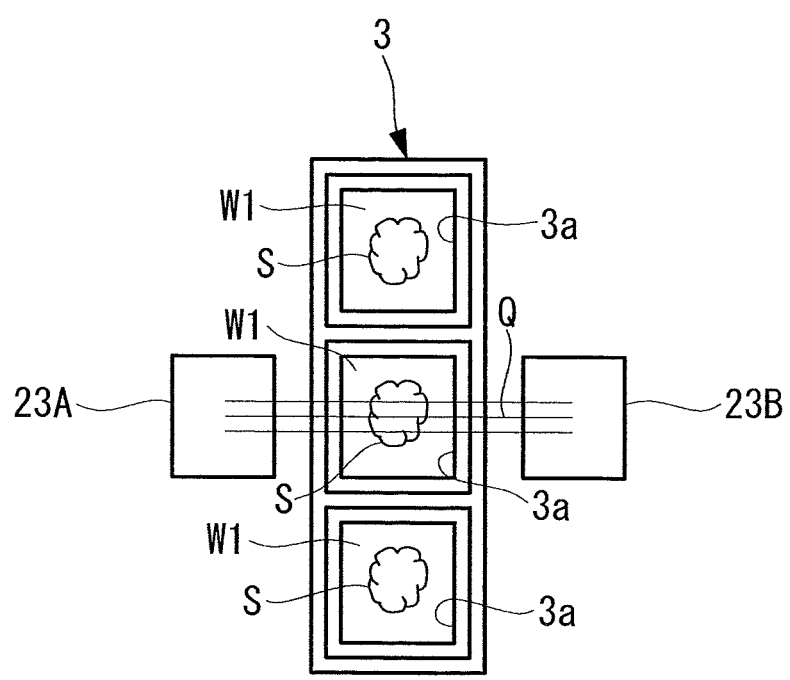
FIG. 2 is a plan view of a cuvette and prisms in FIG. 1, as viewed in a direction along a detection light axis.

As shown in FIG. 2, the cuvette 3 has an array structure formed by arranging, in one direction, three accommodation sections (specimen accommodation sections) 3a for accommodating the samples S. Each of the accommodation sections 3a is filled with a cuvette solution (first liquid immersion medium) W1, such as a transparent solution, and the samples S are immersed in the respective cuvette solutions W1. Each of the samples S is made transparent as a result of being immersed in the cuvette solution W1. In addition, as shown in FIG. 1, the cuvette 3 has, at side wall sections and a bottom section thereof, transparent sections (light transmitting sections) 3b that can transmit a laser beam and fluorescence, respectively.

The chamber 5 has an opening 5a at the top section thereof and has, at the bottom section thereof, a transparent section (a light transmitting section) 5b that can transmit a laser beam and fluorescence. The transparent section 5b is formed in a wide area at the bottom section so as to cover illumination light axes Q of the illumination optical system 9 and the detection light axis P of the immersion objective lens 11. A chamber solution (second liquid immersion medium) W2 having an index of refraction substantially identical to that of the cuvette solution W1 is stored in this chamber 5, and the cuvette 3 is immersed in the chamber solution W2.

The movable stage 7 includes an arm section 7a for holding the cuvette 3 and a support section 7b for supporting the arm section 7a. This movable stage 7 supports the cuvette 3 with the arm section 7a and the support section 7b such that the cuvette 3 is immersed in the chamber solution W2 via the opening 5a of the chamber 5 and that the transparent section 3b at the side wall sections are located on the illumination light axes Q.

In addition, the movable stage 7 can move the held cuvette 3 in the vertical direction (hereinafter, referred to as the Z direction) and in two-dimensional directions (hereinafter, referred to as the X and Y directions) that intersect the vertical direction and that are orthogonal to each other. By doing so, the movable stage 7 can switch the accommodation section 3a of the cuvette 3 placed on the detection light axis P and change the observation position of the sample S in the same accommodation section 3a.

The immersion objective lens 11 is composed by combining many lenses, not shown in the figure. This immersion objective lens 11 is disposed below the chamber 5 adjacently to the transparent section 5b at the bottom section and is placed face up so as to oppose the transparent section 5b. A liquid immersion solution (third liquid immersion medium) W3, such as pure water, is poured into the gap between an upper surface 11a of the lens at the most leading end of the immersion objective lens 11 and the transparent section 5b at the bottom section of the chamber 5, and the liquid immersion solution W3 is held in the gap due to the surface tension thereof.

The targeting section 12 can finely adjust the focal position of the immersion objective lens 11 in a direction along the detection light axis P by finely moving the immersion objective lens 11 in the Z direction, within the range in which the surface tension of the liquid immersion solution W3 acts in the gap between the upper surface 11a of the lens at the most leading end of the immersion objective lens 11 and the transparent section 5b at the bottom section of the chamber 5.

The illumination optical system 9 include: a laser light source 15 for producing a laser beam; an optical fiber 17 for guiding the laser beam emitted from the laser light source 15; convex lenses 19A and 19B for converting the laser beam guided via the optical fiber 17 into a collimated beam; cylindrical lenses (lenses) 21A and 21B for focusing the laser beam converted into a collimated beam by the convex lenses 19A and 19B; and prisms 23A and 23B having mirror-coated reflection surfaces (reflection mirrors) 24A and 24B for reflecting, towards the sample S, the laser beam focused by the cylindrical lenses 21A and 21B.

The optical fiber 17 has two leading end sections 18A and 18B that are branches split off at a longitudinal intermediate point. These leading end sections 18A and 18B are disposed with a space interposed therebetween in a direction intersecting the detection light axis P such that the immersion objective lens 11 lies between the leading end sections 18A and 18B and are placed face-up so as to oppose the transparent section 5b at the bottom section of the chamber 5.

The laser beam emitted from the one leading end section 18A of the optical fiber 17 is reflected at the reflection surface 24A of the prism 23A towards the sample S via the convex lens 19A and the cylindrical lens 21A, and the laser beam emitted from the other leading end section 18B is reflected at the reflection surface 24B of the prism 23B towards the sample S via the convex lens 19B and the cylindrical lens 21B.

The convex lenses 19A and 19B and the cylindrical lenses 21A and 21B are disposed outside the chamber 5 with a space interposed therebetween in a direction intersecting the detection light axis P such that the detection light axis P lies therebetween, and the prisms 23A and 23B are disposed inside the chamber 5 with a space interposed therebetween in a direction intersecting the detection light axis P such that the detection light axis P lies therebetween and are fixed to the internal bottom section.

The cylindrical lenses 21A and 21B have refractive power in one direction orthogonal to the illumination light axes Q. These cylindrical lenses 21A and 21B focus laser beams composed of substantially collimated beams into planar laser beams having predetermined width dimensions equal to the beam diameter dimensions of the substantially collimated beams and form focal points substantially on the detection light axis P of the immersion objective lens 11.

The prisms 23A and 23B reflect, at the reflection surfaces 24A and 24B, the laser beams that have been focused by the cylindrical lenses 21A and 21B into planar laser beams and cause the laser beams to enter the sample S along the same incident plane expanding in a direction orthogonal to the detection light axis P via the transparent section 3b at the side wall sections of the cuvette 3.

The convex lenses 19A and 19B, the cylindrical lenses 21A and 21B, and the reflection surfaces 24A and 24B of the prisms 23A and 23B are pre-adjusted such that the focal positions of the respective laser beams coincide with each other.

The imaging optical system 13 includes: a mirror 25 for reflecting the fluorescence collected by the immersion objective lens 11; an emission filter 27 for removing the laser beam and so forth from the fluorescence reflected by the mirror 25; an image-forming lens 29 for forming an image of the fluorescence that has passed through the emission filter 27; and a camera (image-capturing unit) 31 for acquiring the fluorescence the image of which has been formed by the image-forming lens 29.

The cuvette solution W1 in the cuvette 3, the chamber solution W2 in the chamber 5, the liquid immersion solution W3 between the immersion objective lens 11 and the chamber 5, the transparent sections 3b of the cuvette 3, and the transparent section 5b of the chamber 5 have substantially identical indexes of refraction.

The operation of the microscope 1 with this structure will be described.

In order to observe a sample S with the microscope 1 according to this embodiment, first the cuvette 3 in which the sample S and the cuvette solution W1 are accommodated is supported with the movable stage 7, is immersed in the chamber 5, and is moved to an intended observation position. In the example shown in FIG. 2, the accommodation section 3a at the center of the cuvette 3 is disposed on the detection light axis P of the immersion objective lens 11.

Subsequently, a laser beam is produced in the laser light source 15. The laser beam emitted from the laser light source 15 is guided by the optical fiber 17 and is split at intermediate point, and the laser beams are emitted from the two leading end sections 18A and 18B. Then, the laser beams are converted into collimated beams via the respective convex lenses 19A and 19B, are focused into planar laser beams by the cylindrical lenses 21A and 21B, and enter the transparent section 5b at the bottom section of the chamber 5.

The laser beams that have entered the chamber 5 via the transparent section 5b at the bottom section enter the respective prisms 23A and 23B and are reflected at the reflection surfaces 24A and 24B. Then, the laser beams are made to enter the sample S from two mutually opposing directions intersecting the detection light axis P via the chamber solution W2, the transparent section 3b of the cuvette 3, and the cuvette solution W1.

The transparent section 5b of the chamber 5, the chamber solution W2, the transparent sections 3b of the cuvette 3, and the cuvette solution W1 have substantially identical indexes of refraction, whereby the laser beam radiated by the illumination optical system 9 can be made to enter the sample S without being reflected.

As a result of the planar laser beams entering the sample S, a fluorescent substance in the sample S along the incident plane of the laser beams is excited, thereby causing fluorescence to be produced. Of the fluorescence produced in the sample S, the fluorescence radiated in a direction along the detection light axis P is collected by the immersion objective lens 11 via the cuvette solution W1, the transparent section 3b at the bottom section of the cuvette 3, the chamber solution W2, the transparent section 5b at the bottom section of the chamber 5, and the liquid immersion solution W3.

Also in this case, because the cuvette solution W1, the transparent section 3b at the bottom section of the cuvette 3, the chamber solution W2, the transparent section 5b at the bottom section of the chamber 5, and the liquid immersion solution W3 have substantially identical indexes of refraction, the fluorescence from the sample S can be collected by the immersion objective lens 11 without being reflected.

The fluorescence collected by the immersion objective lens 11 is reflected at the mirror 25, passes through the emission filter 27, and is imaged by the image-forming lens 29 on the imaging plane of the camera 31. By doing so, a cross-sectional image of the sample S is obtained in the camera 31.

By causing the planar laser beams along the incident plane expanding in a direction orthogonal to the detection light axis P of the immersion objective lens 11 to enter the sample S, not only are the focal positions of the cylindrical lenses 21A and 21B made to coincide with the detection light axis P of the immersion objective lens 11 but also the focal plane of the immersion objective lens 11 is made to coincide with the incident plane of the laser beams, and thereby, it is possible to collect, all at once, the fluorescence that is produced in a wide area along the focal plane of the immersion objective lens 11 using the immersion objective lens 11 and to acquire an image of the fluorescence using the camera 31. By doing so, a clear fluorescence image of the observation region in the sample S can be acquired. In addition, because no regions other than the image acquisition plane of the camera 31 are irradiated with a laser beam, a superior three-dimensional stereoscopic image can be obtained by suppressing fluorescence fading.

In this case, even though the observation position of the sample S is changed by moving the cuvette 3 in the chamber 5 using the movable stage 7, the amount of the liquid immersion solution W3 disposed in the gap between the immersion objective lens 11 and the chamber 5 does not change, and hence, it is not necessary to prepare a large amount of the liquid immersion solution W3 or to replenish the liquid immersion solution W3 so frequently, and furthermore the liquid immersion solution W3 can be prevented from running out.

In addition, even if a change in the observation position of the sample S causes a shift to occur in the focal position of the immersion objective lens 11 depending on the refractive index profile in the sample S, this shift in the focal position can be eliminated by finely adjusting, with the targeting section 12, the position in a direction along the detection light axis P of the immersion objective lens 11. By doing so, the desired observation position in the sample S can be observed accurately.

Note that, as a result of the liquid immersion solution W3 having an index of refraction substantially identical to that of the chamber solution W2, it is possible to suppress the occurrence of spherical aberration when the focal point is finely adjusted with the targeting section 12 in a direction along the detection light axis P of the immersion objective lens 11. In addition, as a result of the transparent sections 3b of the cuvette 3 and the transparent section 5b of the chamber 5 having indices of refraction substantially identical to that of the chamber solution W2, it is possible to suppress the occurrence of spherical aberration even if the thicknesses of the transparent sections 3b of the cuvette 3 and the thickness of the transparent section 5b of the chamber 5 vary due to manufacturing errors.

As described above, according to the microscope 1 of this embodiment, even if a shift occurs in the focal position of the immersion objective lens 11 when the observation position of the sample S is changed, the shift in the focal position can be eliminated merely by finely adjusting the immersion objective lens 11 with the targeting section 12 in a direction along the detection light axis P. Therefore, without having to use a complicated and costly adjustment mechanism, such as those of conventional microscopes, where a shift in the focal position of the immersion objective lens is corrected with a scanner, highly reliable observation can be achieved by preventing the liquid immersion solution W3 from running out, while still reducing the amount of the liquid immersion solution W3 and the frequency of replenishment thereof with a simple and inexpensive structure.

In addition, as a result of the illumination optical system 9 causing laser beams to enter the chamber 5 via the transparent section 5b at the bottom section of the chamber 5, the illumination optical system 9, excluding the prisms 23A and 23B, can be disposed below the chamber 5. By doing so, mechanical interference between the movable stage 7 and the cuvette 3 and the illumination optical system 9 can be avoided, thus making it possible to more easily configure the illumination optical system 9 for causing laser beams to enter the sample S from two directions intersecting the detection light axis P of the immersion objective lens 11.

In this embodiment, the illumination optical system 9 simultaneously irradiates the sample S with laser beams from two different directions. Instead of this, single illumination in which the sample S is irradiated with a laser beam only from one direction may be employed. Because absorption and scattering of light occur in the sample S in many cases, irradiation with a plurality of illuminating light beams is more advantageous in terms of illumination uniformity.

In addition, the movable stage 7 may support the cuvette 3 so as to be rotatable about the detection light axis P in the chamber 5. By doing so, laser beams can be made to enter the same observation position in the sample S from different directions merely by rotating the cuvette 3 about the detection light axis P with the movable stage 7. By doing so, it is possible to suppress the influence of scattering in the sample S by reducing the depth at which the laser beam from each of the directions enters the sample S, thereby acquiring a clear fluorescence image. This is more advantageous in the case of single illumination.

This embodiment can be modified as follows.

Figure 3:
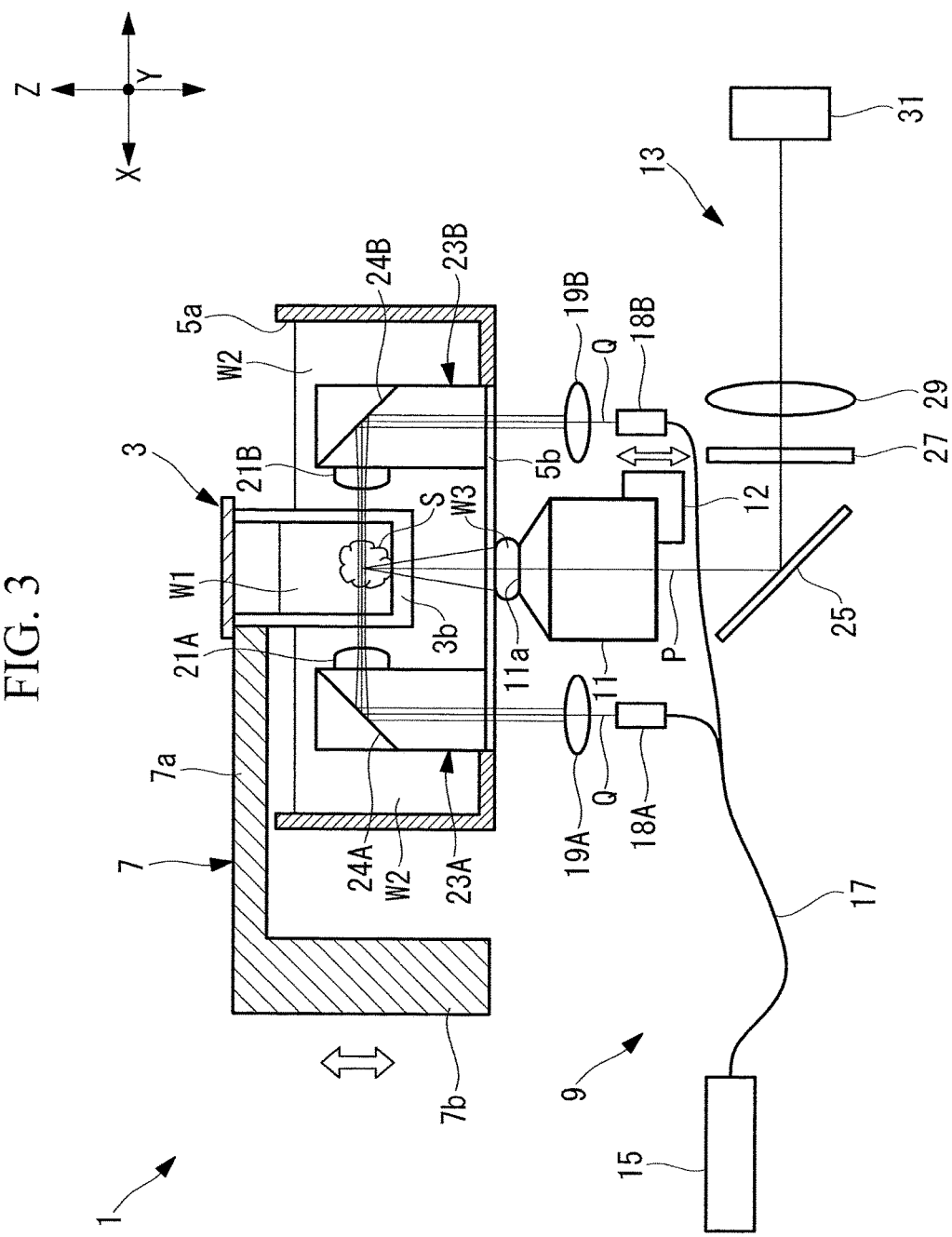
FIG. 3 is a schematic configuration diagram showing a microscope according to a modification of the first embodiment of the present invention.

In this embodiment, the cylindrical lenses 21A and 21B are disposed outside the chamber 5. Instead of this, the cylindrical lenses 21A and 21B may be disposed, for example, inside the chamber 5, as shown in FIG. 3. In this case, it is advisable that the cylindrical lenses 21A and 21B be mounted on, for example, the exit ends of the prisms 23A and 23B.

In order to increase the resolution, it is necessary to set the emission NAs of the cylindrical lenses 21A and 21B to be large and make the planar laser beams thinner. This modification allows the distance from the cylindrical lenses 21A and 21B to the sample S to be shorter than in a case where the cylindrical lenses 21A and 21B are disposed outside the chamber 5. Therefore, it is possible to set the emission NAs of the cylindrical lenses 21A and 21B to be larger and make the planar laser beams thinner. As a result, the resolution can be enhanced with a simple structure that requires nothing more than placing the cylindrical lenses 21A and 21B in the chamber 5.

Second Embodiment

Next, a microscope according to a second embodiment of the present invention will be described.

Figure 4:
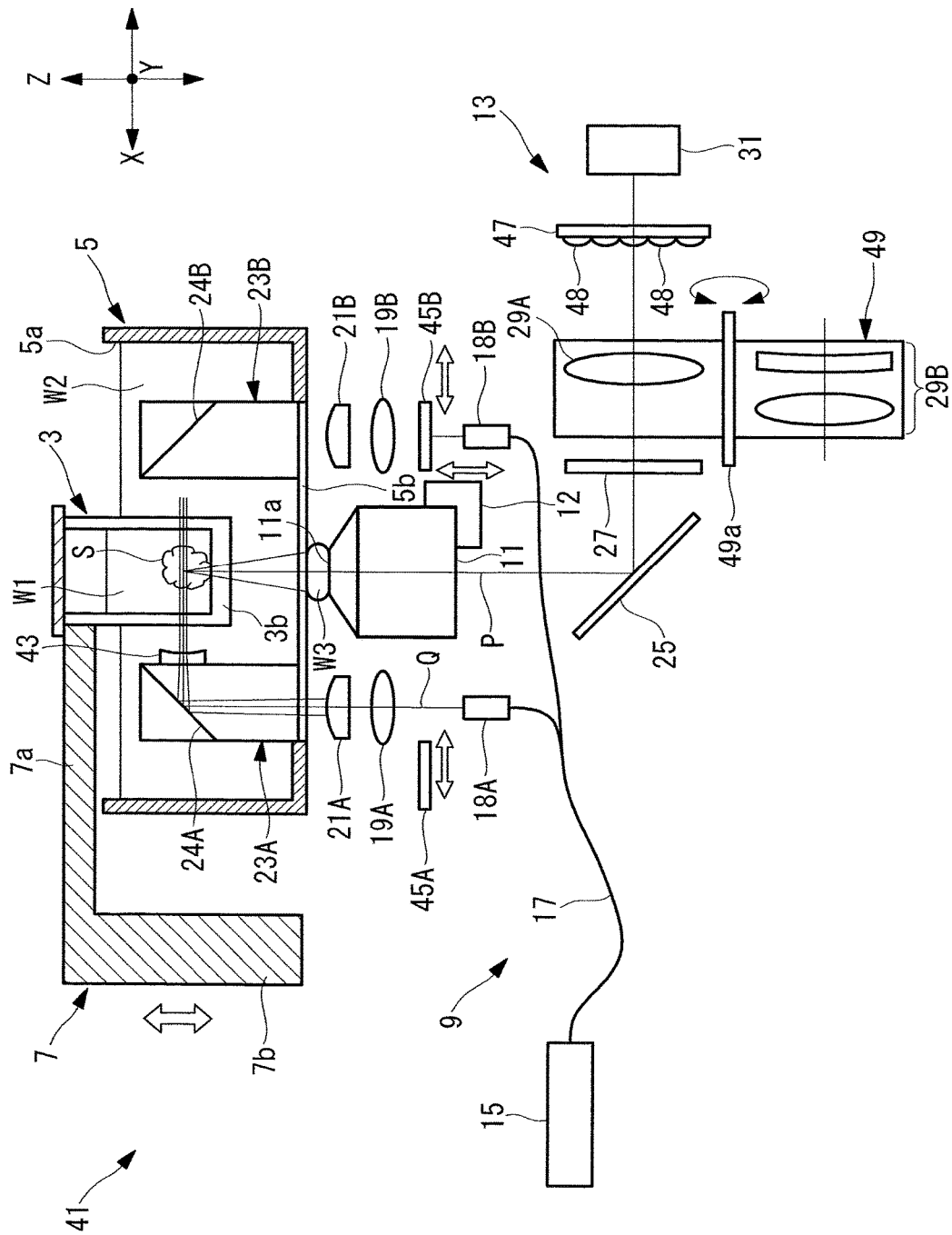
FIG. 4 is a schematic configuration diagram showing a microscope according to a second embodiment of the present invention.

As shown in FIG. 4, a microscope 41 according to this embodiment differs from the microscope according to the first embodiment in that the illumination optical system 9 further includes a cylindrical lens 43 having negative refractive power and shutters 45A and 45B, so that a light-field microscope function or a light-sheet microscope function is alternatively available by switching between the shutters 45A and 45B.

Hereinafter, the structures common to those used in the microscope 1 according to the first embodiment are denoted by the same reference signs, and a description thereof will be omitted.

The cylindrical lens 43 having negative refractive power is disposed, for example, in the optical path of the laser beam emitted from the leading end section 18A of the optical fiber 17 and is mounted on the exit end of the prism 23A. With this cylindrical lens 43, it is possible to form a laser beam that has a rectangular cross section and that has a thickness corresponding to the observation depth in a direction along the detection light axis P of the immersion objective lens 11.

The shutters 45A and 45B are disposed such that they can be inserted into and withdrawn from both the illumination light axes Q of the illumination optical system 9 and are placed between the respective leading end sections 18A and 18B and the respective convex lenses 19A and 19B of the optical fiber 17.

The imaging optical system 13 includes a microlens array 47 composed of a plurality of microlenses 48 disposed in front of the camera 31. The microlenses 48 are two-dimensionally arrayed in directions intersecting the imaging light axis of the camera 31.

In addition, the imaging optical system 13 includes: an image-forming lens 29A for forming an image on the microlens array 47; an image-forming lens 29B for forming an image on the imaging plane of the camera 31; and an image-forming lens turret 49 for holding the image-forming lens 29A and image-forming lens 29B.

The microlens array 47 projects an image onto the imaging plane of the camera 31. By doing so, a plurality of items of image information having different parallaxes can be acquired all at once with the camera 31.

The image-forming lens turret 49 is disposed so as to be rotatable about a rotation axis 49a to allow the image-forming lens 29A and the image-forming lens 29B to be disposed selectively in the optical path of the fluorescence.

The laser light source 15, the optical fiber 17, the convex lens 19A, the cylindrical lens 21A, the prism 23A, and the cylindrical lens 43 of the illumination optical system 9; the immersion objective lens 11; and the mirror 25, the emission filter 27, the image-forming lens 29A, the microlens array 47, and the camera 31 of the imaging optical system 13 function as a light-field microscope. In addition, the laser light source 15, the optical fiber 17, the convex lens 19B, the cylindrical lens 21B, and the prism 23B of the illumination optical system 9; the immersion objective lens 11; and the mirror 25, the emission filter 27, the image-forming lens 29B, and the camera 31 of the imaging optical system 13 function as light-sheet microscope.

The operation of the microscope 41 with this structure will be described.

When a sample S is to be observed using the microscope 41 according to this embodiment, the observation is performed by switching between the light-field microscope function and the light-sheet microscope function by using the shutters 45A and 45B.

When a sample S is to be observed with the light-field microscope function, the shutter 45A is withdrawn from the optical path of the laser beam emitted from the leading end section 18A of the optical fiber 17, and the shutter 45B is inserted onto the optical path of the laser beam emitted from leading end section 18B. In addition, the image-forming lens 29A is inserted onto the imaging light axis of the camera 31 with the image-forming lens turret 49.

In this state, the laser beam emitted from the leading end section 18A of the optical fiber 17 is reflected at the reflection surface 24A of the prism 23A after having passed through the convex lens 19A and the cylindrical lens 21A having positive refractive power, is converted by the cylindrical lens 43 having negative refractive power into a collimated beam having a thickness corresponding to the observation depth in a direction along the detection light axis P of the immersion objective lens 11, and enters the sample S. By making the focal plane of the immersion objective lens 11 coincide with the incident area of the laser beam, the fluorescence produced in a wide area along the focal plane can be acquired all at once with the immersion objective lens 11.

The fluorescence that comes from the sample S and is then collected by the immersion objective lens 11 is imaged on the microlens array 47 with the image-forming lens 29A via the mirror 25 and the emission filter 27, and is projected onto the imaging plane of the camera 31 with the microlenses 48. By doing so, three-dimensional image data can be built from one image by acquiring a plurality of items of image information having different parallaxes all at once.

On the other hand, when a sample S is to be observed with the light-sheet microscope function, the shutter 45A is inserted onto the optical path of the laser beam emitted from the leading end section 18A of the optical fiber 17, and the shutter 45B is withdrawn from the optical path of the laser beam emitted from the leading end section 18B. In addition, the image-forming lens 29B is inserted onto the imaging light axis of the camera 31 with the image-forming lens turret 49. Here, observation with the light-sheet microscope function is performed in the same manner as in the first embodiment, and a description thereof will be omitted.

As described above, according to the microscope 41 of this embodiment, different observation methods can be selected with one inverted microscope. In this case, even though the observation position of the sample S is changed in the chamber 5 by moving the movable stage 7, the shift in the focal position can be eliminated by finely adjusting, with the targeting section 12, the position in a direction along the detection light axis P of the immersion objective lens 11, thereby allowing the desired observation position in the sample to be observed accurately.

This embodiment can be modified as follows.

A first modification may be realized by providing a variable diaphragm in the optical path of the laser beam emitted from the leading end section 18A of the optical fiber 17. By changing the thickness of the illuminating light beam of the laser beam by the use of the variable diaphragm, it is possible to avoid wastefully radiating a laser beam to the depth achieved with the light-field microscope function.

A second modification may be realized by employing, for the light-field microscope function and the light-sheet microscope function, a scanner to allow a laser beam to be scanned in the Z direction, instead of moving the sample S in the Z direction by using the movable stage 7. In this case, because the sample S is not moved in the Z direction, the sample S can be relieved from being subject to stimulation when a living organism is to be observed. Particularly when a change in calcium in a living body is to be imaged, more accurate measurement can be performed by avoiding stimulation of the sample S.

Third Embodiment

Next, a microscope according to a third embodiment of the present invention will be described.

Figure 5:
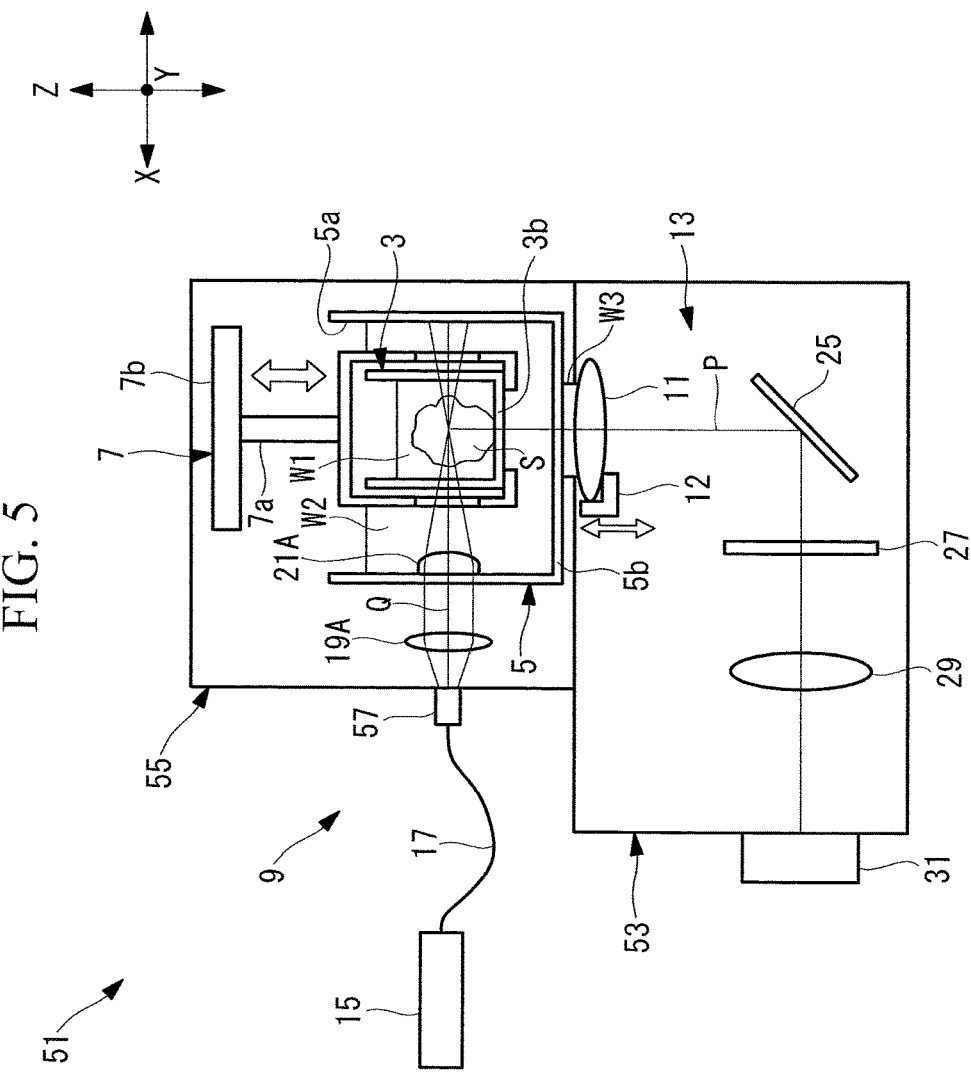
FIG. 5 is a schematic configuration diagram showing a microscope according to a third embodiment of the present invention.

As shown in FIG. 5, a microscope 51 according to this embodiment differs from the microscope according to the first embodiment in that the illumination optical system 9 causes a laser beam to pass through a side wall section of the chamber 5 and then causes the laser beam to enter a sample S.

Hereinafter, the structures common to those used in the microscope 1 according to the first embodiment are denoted by the same reference signs, and a description thereof will be omitted.

The microscope 51 according to this embodiment includes an inverted-microscope configuring section 53, a light-sheet illumination module 55, the laser light source 15, and the optical fiber 17.

The inverted-microscope configuring section 53 includes the immersion objective lens 11, the mirror 25, the emission filter 27, the image-forming lens 29, and the camera 31.

The light-sheet illumination module 55 includes the cuvette 3, the chamber 5, the movable stage 7, the targeting section 12, the convex lens 19A, and the cylindrical lens 21A.

The cuvette 3 and the chamber 5 have transparent sections 3b and 5b, respectively, on the detection light axis P at the bottom face sections and on the illumination light axis Q at the side wall sections. There is an advantage in that this embodiment can be configured in an additional (add-on) manner merely by placing the light-sheet illumination module 55 on the inverted-microscope configuring section 53, which is a conventional inverted microscope.

The exit end of the optical fiber 17 is detachably connected to the light-sheet illumination module 55 via a fiber connector 57, such as an FPC (Flexible Printed Circuit).

When a sample S is observed using the microscope 51 with this structure, the laser beam emitted from the laser light source 15 is guided by the optical fiber 17 and enters the light-sheet illumination module 55 via the fiber connector 57. The laser beam that has entered the light-sheet illumination module 55 is converted into a collimated beam by the convex lens 19A, passes through the transparent section 5b at the side wall section of the chamber 5, and is focused by the cylindrical lens 21A. The laser beam focused by the cylindrical lens 21A passes through the transparent section 3b at the side wall section of the cuvette 3 and enters the sample S.

When the sample S is observed using the microscope 51 according to this embodiment, despite the observation position of the sample S being changed in the chamber 5 by moving the movable stage 7, the shift in the focal position can be eliminated in the same manner by finely adjusting the position in a direction along the detection light axis P of the immersion objective lens 11 by using the targeting section 12. Therefore, a desired observation position in the sample S can be observed accurately.

As described above, according to the microscope 51 of this embodiment, the illumination optical system 9 can be disposed laterally with respect to the chamber 5. In addition, this embodiment can be configured merely by adding the light-sheet illumination module 55, which is provided with the chamber 5, the movable stage 7, the targeting section 12, and the illumination optical system 9, to the inverted-microscope configuring section 53, which is a conventional inverted microscope and is provided with the immersion objective lens 11, the targeting section 12, and the camera 31.

Although this embodiment is configured from a light-sheet microscope, an illumination module for a light-field microscope may be configured.

Fourth Embodiment

Next, a microscope according to a fourth embodiment of the present invention will be described.

Figure 6:
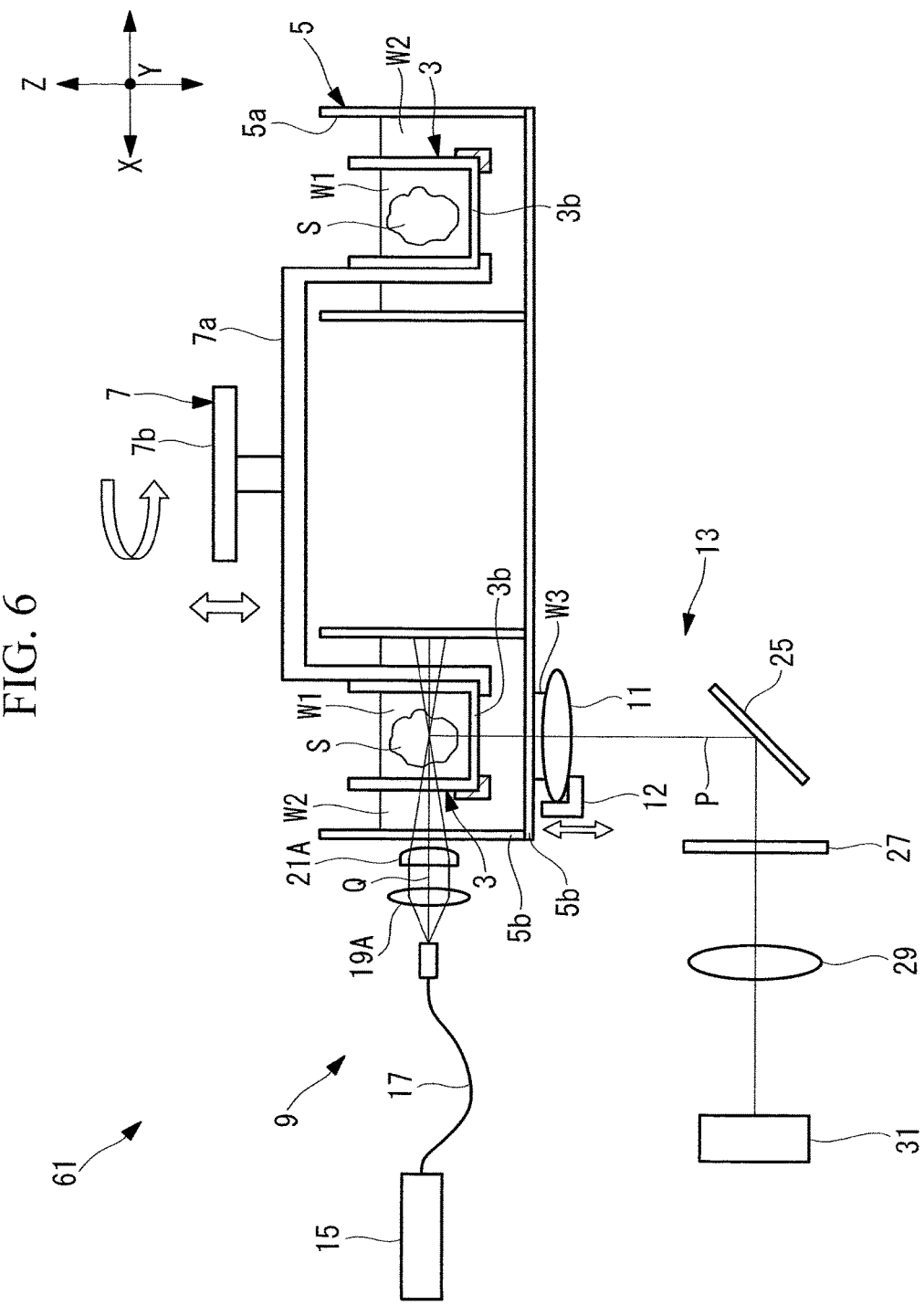
FIG. 6 is a schematic configuration diagram showing a microscope according to a fourth embodiment of the present invention.
Figure 7:
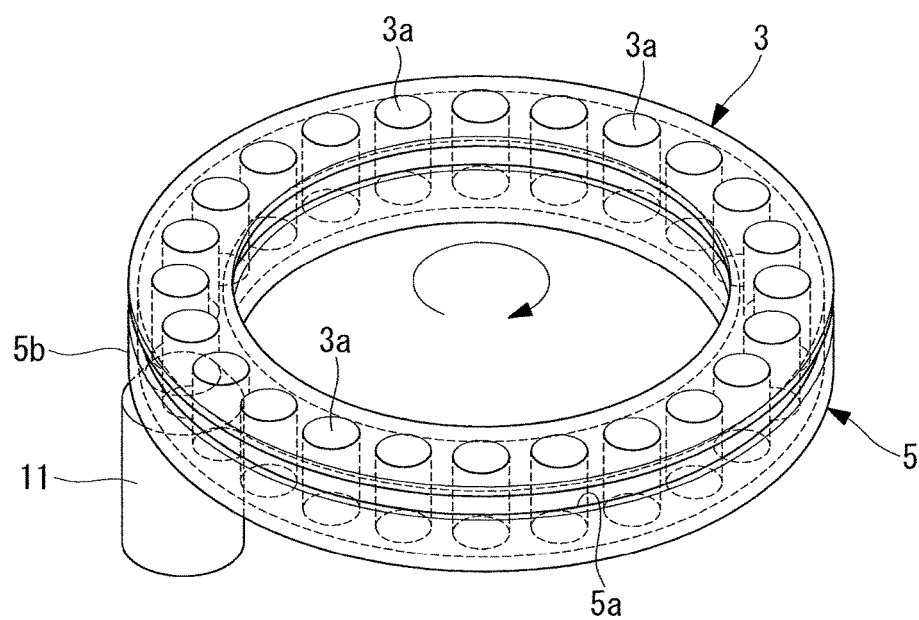
FIG. 7 is a perspective view showing a chamber and a cuvette in FIG. 6

As shown in FIGS. 6 and 7, a microscope 61 according to this embodiment differs from the microscope according to the first embodiment in that the cuvette 3 and the chamber 5 have an annular shape and in that the movable stage 7 supports the cuvette 3 so as to be rotatable about an axis parallel to the detection light axis P.

Hereinafter, the structures common to those used in the microscope 1 according to the first embodiment are denoted by the same reference signs, and a description thereof will be omitted.

Figure 8:
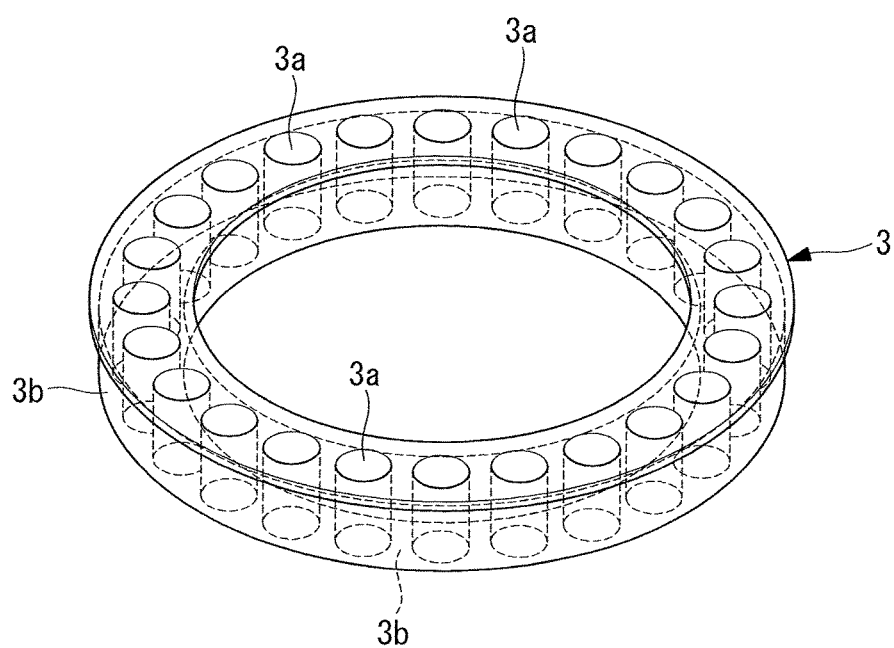
FIG. 8 is a perspective view showing the cuvette in FIG. 6.

As shown in FIG. 8, the cuvette 3 is, for example, a micro plate formed by arranging, along a circumferential direction, a plurality of accommodation sections 3a in which the samples S are accommodated. This cuvette 3 has a transparent section 3b at the side wall section and at the bottom section for each of the accommodation sections 3a. For the cuvette 3 in the example shown in FIG. 8, the side wall section and the bottom section are formed of the transparent sections 3b all along the circumferential direction.

Figure 9:
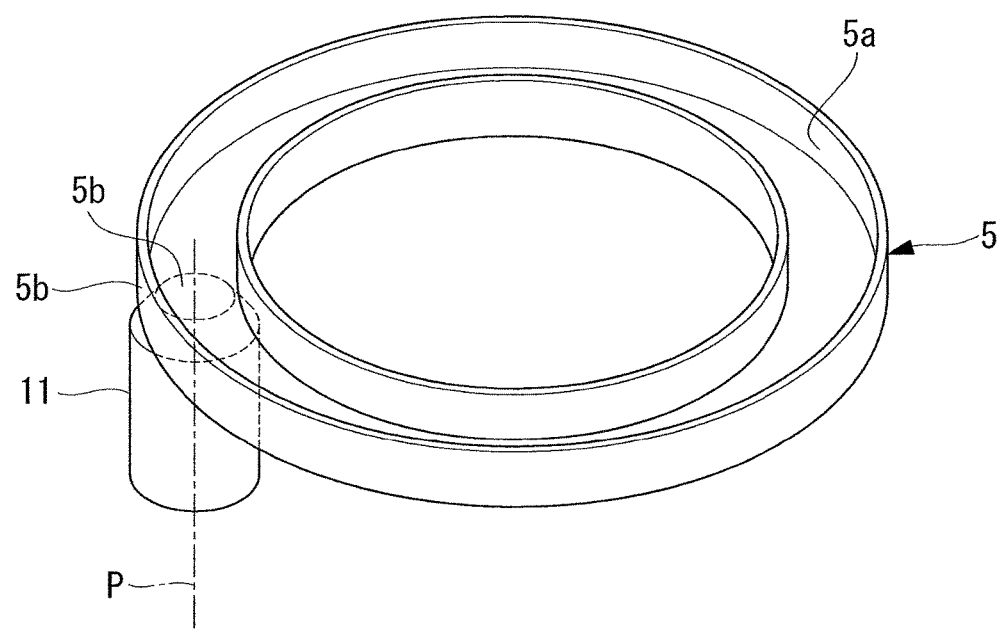
FIG. 9 is a perspective view showing the chamber in FIG. 6.

The chamber 5 has the opening 5a, the inner diameter of which is smaller than the inner diameter of the cuvette 3 and the outer diameter of which is larger than the outer diameter of the cuvette 3. As shown in FIGS. 6 and 9, this chamber 5 has the transparent section 5b, one each on the illumination light axes Q of the illumination optical system 9 at the side wall section and on the detection light axis P of the immersion objective lens 11 at the bottom section. Also in this chamber 5, the side wall section and the bottom section may be formed of the transparent section 5b all along the circumferential direction.

The illumination optical system 9 causes a laser beam to be incident via the transparent section 5b at the side wall section of the chamber 5.

The operation of the microscope 61 with this structure will be described.

When a sample S is observed using the microscope 61 according to this embodiment, the cuvette 3 is rotated with the movable stage 7 about an axis parallel to the detection light axis P to place any one of the accommodation sections 3a on the detection light axis P.

The laser beam emitted from the laser light source 15 in this state is guided by the optical fiber 17, is converted into a collimated beam by the convex lens 19A, is focused into a planar laser beam by the cylindrical lens 21A, and then passes through the transparent section 5b at the side wall section of the chamber 5. The laser beam that has entered the chamber 5 passes through the transparent section 3b at the side wall section of the cuvette 3 and enters the sample S. By doing so, a fluorescence image of the sample S in the accommodation section 3a disposed on the detection light axis P can be acquired.

Subsequently, the cuvette 3 is rotated with the movable stage 7 about an axis parallel to the detection light axis P to place the next adjacent accommodation section 3a on the detection light axis P. Then, the sample S in the next accommodation section 3a placed on the detection light axis P is also irradiated with a laser beam in the same manner to acquire a fluorescence image. Fluorescence images of the samples S accommodated in the accommodation sections 3a are acquired sequentially by switching in this manner so that the accommodation section 3a of the cuvette 3 is placed on the detection light axis P.

As described above, according to the microscope 61 of this embodiment, the sample S to be placed on the detection light axis P can be selected merely by moving, with the movable stage 7, the cuvette 3 about an axis parallel to the detection light axis P. Therefore, images can be acquired sequentially with the camera 31 by causing the illumination optical system 9 to sequentially irradiate the sample S in each of the accommodation sections 3a with a laser beam and sequentially causing the immersion objective lens 11 to collect fluorescence from the sample S in each of the accommodation sections 3a. By doing so, images of a large number of samples S can be acquired in an efficient and fast manner.

This embodiment has been described by way of an example where a micro plate is used as the cuvette 3. Instead of this, a plurality of cuvettes 3 may be arranged, for example, in an array along the circumferential direction. In this case, it is advisable that each of the cuvettes 3 be supported with the movable stage 7 so as to be movable about an axis parallel to the detection light axis P, thereby switching the cuvette 3 to be placed on the detection light axis P.

In addition, although this embodiment has been described by way of example of a light-sheet microscope, the invention may be applied to a light-field microscope.

Fifth Embodiment

Next, a microscope according to a fifth embodiment of the present invention will be described.

Figure 10:
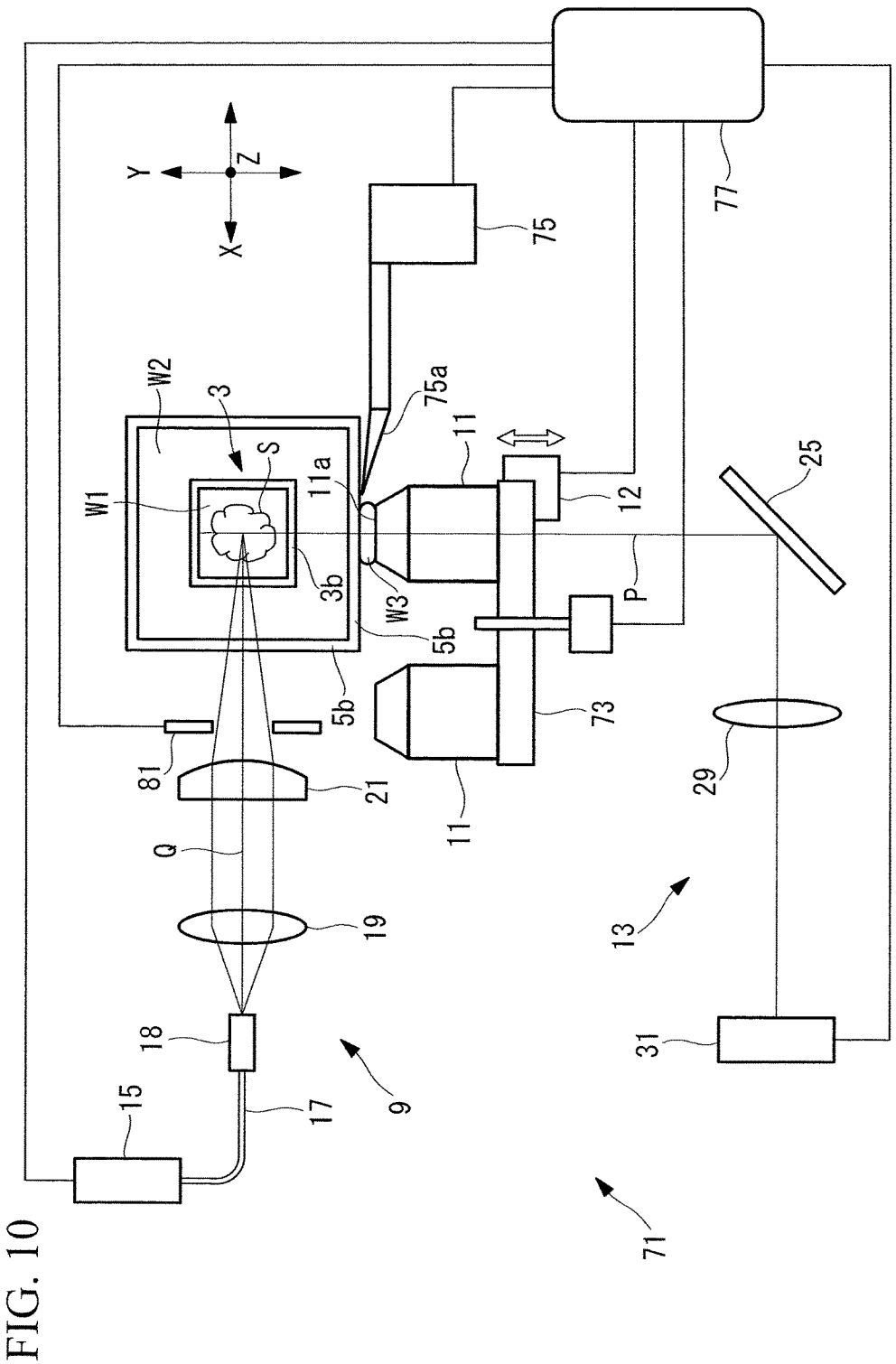
FIG. 10 is a schematic configuration diagram of a microscope according to a fifth embodiment of the present invention, as viewed in the vertical direction.
Figure 11:
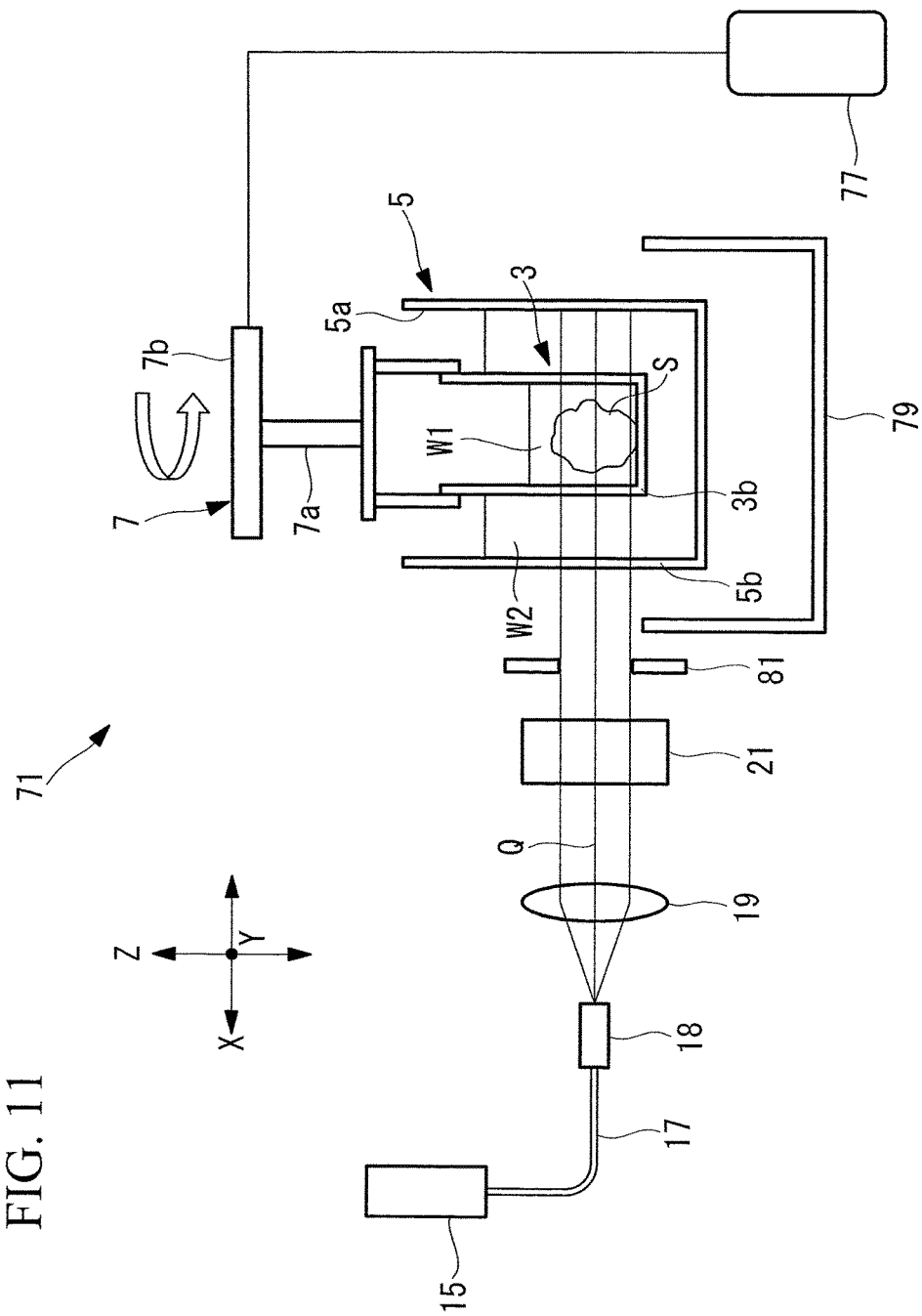
FIG. 11 is a schematic configuration diagram of the microscope in FIG. 10, as viewed in a direction along the detection light axis of an immersion objective lens.

As shown in FIGS. 10 and 11, a microscope 71 according to this embodiment differs from the microscopes according to the first to fourth embodiments in that the illumination optical system 9 is a single illumination system and causes a laser beam to pass through a side wall section of the chamber 5 and to enter a sample S, in that the immersion objective lens 11 collects fluorescence coming from the sample S via a side wall section of the chamber 5, and in that the movable stage 7 supports the cuvette 3 such that the cuvette 3 can be moved in the X, Y, and Z directions and rotated about a predetermined rotation axis orthogonal to the illumination light axis Q and the detection light axis P in the chamber 5.

Hereinafter, the structures common to those used in the microscopes 1, 41, 51, and 61 according to the first to fourth embodiments are denoted by the same reference signs, and a description thereof will be omitted.

The microscope 71 includes: the cuvette 3; the chamber 5; the movable stage 7; the illumination optical system 9; a plurality of the immersion objective lenses 11 having different magnifications; a revolver 73 for supporting the plurality of immersion objective lenses 11; the targeting section 12 for moving the immersion objective lenses 11 supported by the revolver 73 in a direction along the detection light axis P; the imaging optical system 13; a water replenishing device 75 for replenishing the liquid immersion solution W3; and a control device 77 for controlling the movable stage 7 and so forth. In FIG. 11, reference sign 79 denotes a drain tank.

In this embodiment, the cuvette 3 is a single storage container filled with the cuvette solution W1, and the sample S is immersed in the cuvette solution W1. In addition, as shown in FIG. 10, the cuvette 3 has a transparent section (light transmitting section) 3b on each of all the side wall sections in the peripheral direction.

The chamber 5 has transparent sections (light transmitting sections) 5b on two side wall sections adjacent to each other.

The illumination optical system 9 includes: the laser light source 15; the optical fiber 17; a convex lens 19 for converting the laser beam guided by the optical fiber 17 into a collimated beam; a cylindrical lens 21 having the same structure as the cylindrical lenses 21A and 21B; and a variable diaphragm 81.

The variable diaphragm 81 is disposed between the cylindrical lens 21 and the transparent section 5b at the side wall section of the chamber 5. The thickness of the laser beam focused into a planar laser beam by the cylindrical lens 21 can be changed by changing the beam diameter of the laser beam using the variable diaphragm 81. This change is performed according to the immersion objective lens 11 inserted onto the optical path.

A leading end section 18 of the optical fiber 17, the convex lens 19, the cylindrical lens 21, and the variable diaphragm 81 are disposed so as to face the transparent section 5b at one of the side wall sections of the chamber 5, and the laser beam emitted from laser light source 15 is made to enter the sample S via the transparent section 5b at the one side wall section of the chamber 5 and via the transparent section 3b at one of the side wall sections of the cuvettes 3.

As shown in FIG. 10, the immersion objective lenses 11 are disposed outside the chamber 5, with the detection light axes P thereof being orthogonal to the illumination light axis Q, so as to face the transparent section 5b at the other side wall section. The liquid immersion solution W3, such as pure water, is poured in the gap between the upper surface 11a of the lens at the most leading end of an immersion objective lens 11 and the transparent section 5b at the other side wall section of the chamber 5, and the liquid immersion solution W3 is held in the gap due to the surface tension.

The revolver 73 can selectively place the plurality of immersion objective lenses 11 on the optical path of the fluorescence to be detected. By doing so, the immersion objective lens 11 to be used can be selected, for example, according to the purpose of observation.

The water replenishing device 75 has a nozzle 75a at the leading end section thereof and, when switching the immersion objective lens 11, can replenish the liquid immersion solution W3 from the nozzle 75a into the gap between the upper surface 11a of the lens at the most leading end of the immersion objective lens 11 and the transparent section 5b at the side wall section of the chamber 5.

The imaging optical system 13 includes the mirror 25, the image-forming lens 29 for forming an image of fluorescence reflected at the mirror 25, and the camera 31.

Using the movable stage 7, the control device 77 controls movement of the cuvette 3 in the X, Y, and Z directions and rotation of the cuvette 3 about a predetermined rotation axis.

In addition, the control device 77 controls the laser light source 15 and the camera 31 and controls: adjustment of the beam diameter of a laser beam with the variable diaphragm 81; switching among the immersion objective lenses 11 with the revolver 73; fine adjustment of the position in a direction along the detection light axis P of the immersion objective lens 11 with the targeting section 12; and replenishment of the liquid immersion solution W3 with the water replenishing device 75.

The operation of the microscope 71 with this structure will be described.

In order to observe a sample S with the microscope 71 according to this embodiment, the control device 77 is used to cause the cuvette 3 in which the sample S and the cuvette solution W1 are accommodated to be supported by the movable stage 7 and to be immersed in the chamber solution W2 in the chamber 5, and then causes a laser beam to be produced from the laser light source 15.

The laser beam emitted from the laser light source 15 is guided by the optical fiber 17, is converted into a collimated beam by the convex lens 19, is focused into a planar laser beam by the cylindrical lens 21, passes through the variable diaphragm 81, and enters the chamber 5 after having passed through the transparent section 5b at the side wall section of the chamber 5.

The laser beam that has entered the chamber 5 enters the sample S from a direction orthogonal to the detection light axis P via the chamber solution W2, the transparent section 3b at the side wall section of the cuvette 3, and the cuvette solution W1. As a result of the planar laser beam entering the sample S, the fluorescent substance in the sample S is excited along the incident plane of the laser beam, thereby producing fluorescence.

Of the fluorescent produced in the sample S, the fluorescence radiated in a direction along the detection light axis P is collected by the immersion objective lens 11 via the cuvette solution W1, the transparent section 3b at the side wall section of the cuvette 3, the chamber solution W2, the transparent section 5b at the side wall section of the chamber 5, and the liquid immersion solution W3.

The fluorescence collected by the immersion objective lens 11 is reflected at the mirror 25 and is imaged by the image-forming lens 29 onto the imaging plane of the camera 31. By doing so, a cross-sectional image of the sample S orthogonal to the detection light axis P is obtained in the camera 31. By moving the cuvette 3 in the X, Y, and Z directions in the chamber 5 by driving the movable stage 7 with the control device 77 so as to change the observation position of the sample S, a cross-sectional image at each of the observation positions can be acquired.

By making the focal position of the cylindrical lens 21 coincide with the detection light axis P of the immersion objective lens 11 and also making the focal plane of the immersion objective lens 11 coincide with the incident plane of the laser beam, fluorescence produced in a wide area along the focal plane of the immersion objective lens 11 can be imaged with the camera 31 by collecting the fluorescence all at once with the immersion objective lens 11, thereby making it possible to acquire a clear fluorescence image of the observation region in the sample S. In addition, because no regions other than the image acquisition plane of the camera 31 are irradiated with a laser beam, a superior three-dimensional stereoscopic image can be obtained by suppressing fluorescence fading.

In this case, according to the microscope 71 of this embodiment, a superior image can be acquired over substantially the entire area of the sample S by driving the movable stage 7 using the control device 77 so as to rotate the cuvette 3 about a predetermined rotation axis orthogonal to the illumination light axis Q and detection light axis P, thereby inverting the orientation of the sample S relative to the immersion objective lens 11 so as to bring parts that have been far away from the immersion objective lens 11 of the sample S close to the immersion objective lens 11.

In addition, despite the observation position of the samples S being changed by moving the cuvette 3 in the chamber 5 using the movable stage 7, the amount of the liquid immersion solution W3 disposed in the gap between the immersion objective lens 11 and the chamber 5 does not change (remains held as is due to the surface tension, irrespective of the focal point being finely adjusted), and therefore it is not necessary to prepare a large amount of the liquid immersion solution W3 or replenish the liquid immersion solution W3 so frequently, and furthermore the liquid immersion solution W3 can be prevented from running out.

In addition, even though there occurs a shift in the focal position of the immersion objective lens 11 depending on the refractive index profile in the sample S or a shift in the focal position of the immersion objective lens 11 due to a slight difference between the index of refraction of the cuvette solution W1 and the index of refraction of the chamber solution W2 when the observation position of the sample S is changed, the shift in the focal position can be eliminated merely by finely adjusting the position in a direction along the detection light axis P of the immersion objective lens 11 using the targeting section 12.

Although this embodiment has been described by way of an example of a light-sheet microscope describe, the invention may be applied to a light-field microscope. In this case, it is advisable that the illumination optical system 9 further include the cylindrical lens 43 having negative refractive power, in the same manner as in the second embodiment (refer to FIG. 4), and that the cylindrical lens 43 be placed between the cylindrical lens 21 and the chamber 5, thereby causing a laser beam having a thickness in a direction along the imaging light axis of the camera 31 to enter the sample S. It is also advisable that the imaging optical system 13 include the microlens array 47 composed of the plurality of microlenses 48 for projecting an image onto the imaging plane of the camera 31 and the image-forming lens 29A (also refer to FIG. 4) for forming an image on the microlens array 47. By doing so, a plurality of items of image information having different parallaxes can be acquired all at once.

Sixth Embodiment

Next, a microscope according to a sixth embodiment of the present invention will be described.

Figure 12:
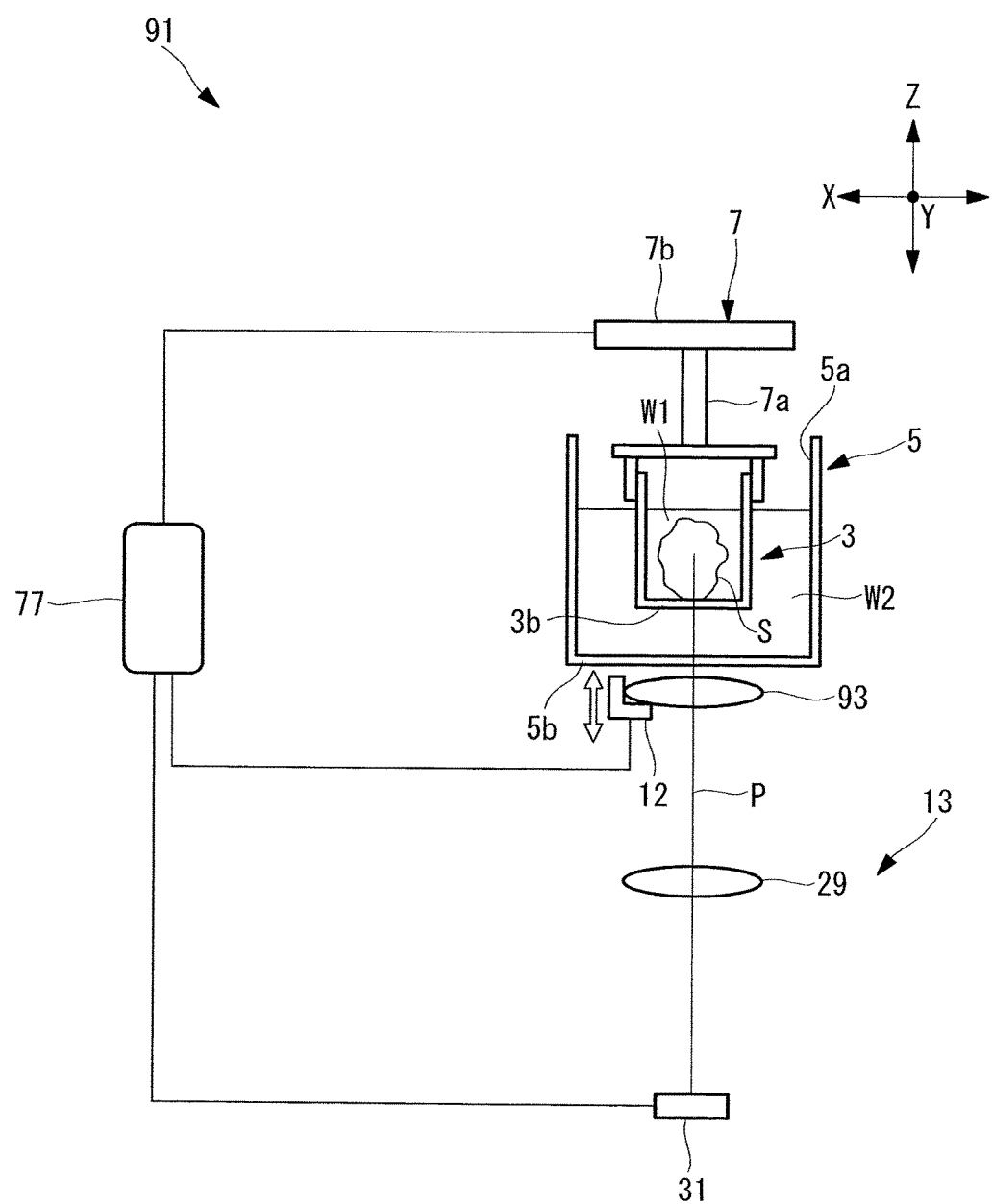
FIG. 12 is a schematic configuration diagram showing a microscope according to a sixth embodiment of the present invention.

As shown in FIG. 12, a microscope 91 according to this embodiment differs from the microscopes according to the first to fifth embodiments in that the microscope 91 constitutes a luminescence microscope.

Hereinafter, the structures common to those used in the microscopes 1, 41, 51, 61, and 71 according to the first to fifth embodiments are denoted by the same reference signs, and a description thereof will be omitted.

The microscope 91 includes: the cuvette 3; the chamber 5; the movable stage 7; a dry objective lens (objective lens) 93 for collecting fluorescence emitted from a sample S; the targeting section 12 that can move the dry objective lens 93 in a direction along the detection light axis P thereof; the imaging optical system 13 for acquiring an image of the sample S on the basis of the fluorescence collected by the dry objective lens 93; and the control device 77 for controlling the movable stage 7 and so forth.

In this embodiment, the cuvette 3 has, at the bottom section thereof, a transparent section (light transmitting section) 3b that can transmit fluorescence.

The chamber 5 has, at the bottom section thereof, a transparent section (light transmitting section) 5b that can transmit fluorescence.

The dry objective lens 93 is disposed outside the chamber 5 adjacently to the transparent section 5b at the bottom section and is placed face up so as to oppose the transparent section 5b. In addition, the dry objective lens 93 is disposed with a space, instead of the liquid immersion solution W3, interposed between the dry objective lens 93 itself and the transparent section 5b at the bottom section of the chamber 5.

The imaging optical system 13 includes the image-forming lens 29 for forming an image of the fluorescence collected by the dry objective lens 93 and a camera 31.

The operation of the microscope 91 with this structure will be described.

In order to observe a sample S using the microscope 91 according to this embodiment, the cuvette 3 in which the sample S and the cuvette solution W1 are accommodated is supported by the movable stage 7, is immersed in the chamber solution W2 in the chamber 5, and is moved to the intended observation position.

Of the fluorescent self-emitted by the sample S, the fluorescence radiated in a direction along the detection light axis P is collected by the dry objective lens 93 via the cuvette solution W1, the transparent section 3b at the bottom section of the cuvette 3, the chamber solution W2, and the transparent section 5b at the bottom section of the chamber 5, and is then imaged by the image-forming lens 29 on the imaging plane of the camera 31. By doing so, a cross-sectional image of the sample S orthogonal to the detection light axis P is obtained in the camera 31. By moving the cuvette 3 in the X, Y, and Z directions in the chamber 5 by driving the movable stage 7 with the control device 77 so as to change the observation position of the sample S, a cross-sectional image at each of the observation positions can be acquired.

In this case, according to the microscope 91 of this embodiment, even though there occurs a shift in the focal position of the dry objective lens 93 depending on the refractive index profile in the sample S or a shift in the focal position of the dry objective lens 93 due to a slight difference between the index of refraction of the cuvette solution W1 and the index of refraction of the chamber solution W2 when the observation position of the sample S is changed by moving the cuvette 3 in the chamber 5, the shift in the focal position can be eliminated merely by finely adjusting the dry objective lens 93 in a direction along the detection light axis P by using the targeting section 12.

Therefore, despite even a slight difference in refractive index profile in the sample S or in index of refraction between the cuvette solution W1 and the chamber solution W2, equi-distant images can be obtained by performing slight fine adjustment when stacked images, which are acquired by driving the movable stage 7 in the Z direction at equal distances, are to be obtained, thereby making it possible to build a distortion-free three-dimensional image. In addition, the structure can be made all the more simple and inexpensive because no light sources or illumination optical systems are required.

Although the embodiments of the present invention have been described in detail with reference to the drawings, the specific structure is not limited to those of these embodiments but includes design changes etc. that do not depart from the spirit of the present invention. The present invention is not limited to the invention applied to each of the above-described embodiments and modifications but can be applied to, for example, embodiments in which these embodiments and modifications are appropriately combined and is not particularly limited. For example, although the above-described embodiments have been described by way of examples where a laser beam is made to enter the sample S from one direction or two directions, a laser beam may be made to enter the sample S from, for example, three or more directions.

In addition, in each of the above-described embodiments, all of the cuvette solution W1, the chamber solution W2, the liquid immersion solution W3, the transparent section 3b of the cuvette 3, and the transparent section 5b of the chamber 5 have substantially the same index of refraction. However, it is sufficient if at least the cuvette solution W1 and the chamber solution W2 have indices of refraction substantially identical to each other because the indices of refraction of the transparent section 3b of the cuvette 3 and of the transparent section 5b of the chamber 5 through which light and fluorescence pass do not change even though the cuvette 3 is moved in the chamber, as long as each of the thickness of the transparent section 3b of the cuvette 3 and the thickness of the transparent section 5b of the chamber 5 is constant.

From the above-described embodiment, the following invention is derived.

One aspect of the present invention is a microscope including: a medium container that stores a second liquid immersion medium in which a specimen container accommodating a first liquid immersion medium together with a specimen is immersed and that has an index of refraction identical to that of the first liquid immersion medium; an objective lens that is placed outside the medium container and that collects light emitted from the specimen; an image-capturing unit that acquires an image of the light collected by the objective lens; a targeting section that moves a focal position of the objective lens in a direction along a detection light axis thereof; and a movable stage that supports the specimen container in the medium container such that the specimen container can move at least in a direction along the detection light axis, wherein each of the specimen container and the medium container has a light-transmitting section capable of transmitting the light from the specimen, and the objective lens is disposed so as to face the light-transmitting section of the specimen container, with the light-transmitting section of the medium container interposed therebetween.

According to this aspect, the specimen is accommodated in the specimen container with the first liquid immersion medium, and then the specimen container as a whole is immersed into the second liquid immersion medium in the medium container. Thereafter, the light emitted from the specimen passes through the first liquid immersion medium, the light-transmitting section of the specimen container, the second liquid immersion medium having an index of refraction identical to that of the first liquid immersion medium, and the light-transmitting section of the medium container, is collected by the objective lens, and is imaged by the image-capturing unit. Therefore, by moving the specimen container in the medium container in a direction along the detection light axis of the objective lens by using the movable stage, a cross-sectional image of the specimen intersecting the detection light axis of the objective lens can be acquired.

In this case, even though the observation position is changed by moving the specimen container in the medium container by using the movable stage, the relative position between the objective lens and the medium container does not change. Therefore, even though the liquid immersion medium is held between the leading end of the objective lens and the light-transmitting section of the medium container, the movement of the specimen container does not cause the amount of this liquid immersion medium to change. Therefore, it is not necessary to prepare a large amount of the liquid immersion medium between the leading end of the objective lens and the light-transmitting section of the medium container or replenish the liquid immersion medium so frequently. Furthermore, this liquid immersion medium does not run out.

In addition, even if a shift occurs in the focal position of the objective lens according to the refractive index profile in the specimen when the observation position of the specimen is changed, the shift in the focal position can be eliminated by finely adjusting the position in a direction along the detection light axis of the objective lens using the targeting section.

Therefore, it is possible to configure a microscope that can prevent the liquid immersion medium from running out while still reducing the amount of the liquid immersion medium and the replenishment frequency thereof with a simple and inexpensive structure, thereby achieving highly reliable observation.

In the above-described aspect, the objective lens may be disposed with a space interposed between the objective lens and the light-transmitting section of the medium container.

With this structure, the, objective lens can be switched to another with a different magnification.

In the above-described aspect, the objective lens may be an immersion objective lens, and the immersion objective lens may be disposed with a third liquid immersion medium interposed between the immersion objective lens and the light-transmitting section of the medium container.

With this structure, by employing a medium having an index of refraction larger than that of air as the third liquid immersion medium, the numerical aperture (NA) of the immersion objective lens can be increased, thereby making it possible to obtain higher resolution. In addition, because movement of the specimen container does not cause the amount of the third liquid immersion medium to change, it is not necessary to prepare a large amount of the third liquid immersion medium or replenish the third liquid immersion medium so frequently. Furthermore, the third liquid immersion medium does not run out.

In the above-described aspect, the immersion objective lens may be disposed with the detection light axis oriented in a direction intersecting a vertical direction, and the third liquid immersion medium may be held between the immersion objective lens and the light-transmitting section of the medium container due to surface tension.

With this structure, no mechanism for holding the third liquid immersion medium between the leading end of the immersion objective lens and the light-transmitting section of the medium container is required, and hence the configuration can be simple.

In the above-described aspect, the specimen container and the medium container may have the light-transmitting sections at side wall sections, and the immersion objective lens may be disposed with the detection light axis oriented in a direction substantially orthogonal to the vertical direction.

With this structure, the immersion objective lens can be placed laterally with respect to the medium container, adjacently to the light-transmitting section at the side wall section with the third liquid immersion medium interposed therebetween.

In the above-described aspect, the third liquid immersion medium may have an index of refraction identical to that of the second liquid immersion medium.

With this structure, it is possible to suppress the occurrence of spherical aberration even though a change in the observation position of the specimen causes a shift in the focal position of the immersion objective lens depending on the refractive index profile in the specimen and hence the focal point is finely adjusted in a direction along the detection light axis of immersion objective lens by using the targeting section.

In the above-described aspect, the light-transmitting section of the specimen container may have an index of refraction identical to that of the second liquid immersion medium.

With this structure, even if the thickness of the light-transmitting section of the specimen container varies due to manufacturing errors, it is possible to suppress the occurrence of spherical aberration.

In the above-described aspect, the light-transmitting section of the medium container may have an index of refraction identical to that of the second liquid immersion medium.

With this structure, even if the thickness of the light-transmitting section of the medium container varies due to manufacturing errors, it is possible to suppress the occurrence of spherical aberration.

In the above-described aspect, the movable stage may support the specimen container so as to be movable in a direction intersecting the detection light axis.

With this structure, the observation position of the specimen can be changed in a direction intersecting the detection light axis of the objective lens.

In the above-described aspect, the image-capturing unit may acquire an image of the light self-emitted by the specimen.

With this structure, a luminescence microscope can be configured, and therefore, the configuration can be made all the more simple and inexpensive because no light source or illumination optical system is required.

The above-described aspect may include an illumination optical system that irradiates the specimen with light from a direction intersecting the detection light axis, wherein each of the specimen container and the medium container may have a light transmitting section that transmits, towards the specimen, the light coming from the illumination optical system.

With this structure, by placing the illumination optical system laterally with respect to the medium container, the specimen can be irradiated with the light emitted by the illumination optical system, from the sides of the medium container and the specimen container and via each of the light transmitting sections.

In the above-described aspect, the medium container may have the light transmitting section at a bottom section, and the illumination optical system may include a reflection mirror placed in the medium container and may cause the light to enter the medium container via the light transmitting section at the bottom section and to reflect the light at the reflection mirror towards the specimen.

With this structure, the illumination optical system, excluding the reflection mirror, can be placed below the medium container. By doing so, it is possible to avoid mechanical interference between the movable stage and the specimen container and the illumination optical system, thereby making it easier to configure an illumination optical system that can irradiate the specimen with light not only from one direction but also from a plurality of directions intersecting the detection light axis of the objective lens.

In the above-described aspect, the medium container may have the light transmitting section at a side wall section, and the illumination optical system may cause the light to enter the medium container via the light transmitting section at the side wall section.

With this structure, the illumination optical system can be placed laterally with respect to the medium container. By doing so, the microscope can be configured merely by adding a medium container, a movable stage, and an illumination optical system to a conventional inverted microscope provided with an objective lens, a targeting section, and an image-capturing unit.

In the above-described aspect, the illumination optical system may include a lens that is placed in the medium container and that has positive refractive power.

In order to increase the resolution by reducing the thickness of the light-sheet illumination, the emission NA of the lens needs to be set to be larger. With this structure, because the distance from the lens to the specimen can be made short compared with a case where the lens is placed outside the medium container, the emission NA of the lens can be set to be larger. By doing so, the resolution can be enhanced with a simple structure that requires nothing more than placing a lens having positive refractive power in the medium container.

In the above-described aspect, the lens having positive refractive power may be a cylindrical lens having positive refractive power in one direction intersecting an illumination light axis of the illumination optical system.

With this structure, the light can be focused by the cylindrical lens into the form of a flat surface along a plane intersecting the detection light axis of the detection optical system and made to enter the specimen. In this manner, by making the focal plane of the objective lens coincide with the incident plane of the light, the light produced in a wide area along the focal plane can be collected all at once by the objective lens, thereby making it possible to acquire an image with higher resolution.

The above-described aspect may include a microlens array formed by two-dimensionally arranging a plurality of microlenses in directions intersecting an imaging light axis of the image-capturing unit, wherein the illumination optical system may cause the light in the form of a substantially collimated beam to enter the specimen.

With this structure, by making the focal plane of the objective lens coincide with the incident area of the light, the light produced in a wide area along the focal plane can be collected all at once by the objective lens. Then, a plurality of items of image information having different parallaxes can be obtained all at once by acquiring, with the image-capturing unit, an image projected by the microlens array.

In the above-described aspect, the movable stage may support a plurality of the specimen containers so as to be movable in the medium container about an axis parallel to the detection light axis.

With this structure, the specimen container placed on the detection light axis can be switched merely by moving, with the movable stage, the plurality of specimen containers about an axis parallel to the detection light axis. Therefore, successive acquisition of images with the image-capturing unit is possible by sequentially radiating, with the illumination optical system, light onto the specimen in each of the specimen containers and sequentially collecting, with objective lens, light from the specimen in each of the specimen containers. By doing so, images of a large number of specimens can be acquired in an efficient and fast manner.

In the above-described aspect, the specimen container may have a plurality of specimen accommodation sections arranged in one direction intersecting the illumination light axis of the illumination optical system, and the movable stage may support the specimen accommodation sections so as to be capable of switching the specimen accommodation section placed on the detection light axis.

With this structure, a plurality of specimens can be sequentially observed merely by switching the specimen accommodation section placed on the detection light axis of the objective lens with the movable stage.

In the above-described aspect, the movable stage may support the specimen container so as to be rotatable in the medium container about the detection light axis.

With this structure, merely by rotating the specimen container about the detection light axis with the movable stage, light can be made incident on the same observation position in the specimen from different directions. By doing so, the influence of scattering on the specimen can be suppressed by reducing the depth at which the light enters the specimen from the directions, thereby acquiring a sharp image.

In the above-described aspect, the illumination optical system may cause the light in a flat shape to enter the specimen along a plane intersecting the detection light axis of the objective lens.

With this structure, it is possible to configure a light-sheet microscope that can acquire an image with higher resolution by making the focal plane of the objective lens coincide with the incident plane of the light and collecting, all at once with the objective lens, the fluorescence produced in a wide area along the focal plane of the objective lens.

REFERENCE SIGNS LIST

1, 41, 51, 61, 71, 91 Microscope
3 Cuvette (specimen container)
3a Accommodation section (specimen accommodation section)
3b, 5b Transparent section (light transmitting section)
5 Chamber (medium container)
5a Opening
7 Movable stage
9 Illumination optical system
11 Immersion objective lens (objective lens)
12 Targeting section
31 Camera (image-capturing unit)
21 Cylindrical lens (lens)
21A, 21B Cylindrical lens (lens)
24A, 24B Reflection surface (reflection mirror)
47 Microlens array
93 Dry objective lens (objective lens)
P Detection light axis
Q Illumination light axis
S Sample (specimen)
W1 Cuvette solution (first liquid immersion medium)
W2 Chamber solution (second liquid immersion medium)
W3 Liquid immersion solution (third liquid immersion medium)

The invention claimed is:

1. A microscope comprising:
a medium container that stores a second liquid immersion medium in which a specimen container accommodating a first liquid immersion medium together with a specimen is immersed, the second liquid immersion medium having an index of refraction identical to that of the first liquid immersion medium;
an objective lens that is placed outside the medium container and that collects light emitted from the specimen;
an image-capturing unit that acquires an image of the light collected by the objective lens;
a targeting section that moves a focal position of the objective lens in a direction along a detection light axis thereof; and
a movable stage that supports the specimen container in the medium container such that the specimen container can move at least in a direction along the detection light axis,
wherein each of the specimen container and the medium container has a light-transmitting section capable of transmitting the light from the specimen, and
wherein the objective lens is disposed so as to face the light-transmitting section of the specimen container, with the light-transmitting section of the medium container interposed therebetween.

2. The microscope according to claim 1, wherein the objective lens is disposed with a space interposed between the objective lens and the light-transmitting section of the medium container.

3. The microscope according to claim 1, wherein the objective lens is an immersion objective lens, and the immersion objective lens is disposed with a third liquid immersion medium interposed between the immersion objective lens and the light-transmitting section of the medium container.

4. The microscope according to claim 3, wherein:
the immersion objective lens is disposed with the detection light axis oriented in a direction intersecting a vertical direction, and
the third liquid immersion medium is held between the immersion objective lens and the light-transmitting section of the medium container due to surface tension.

5. The microscope according to claim 4, wherein:
the specimen container and the medium container have the light-transmitting sections at side wall sections, and
the immersion objective lens is disposed with the detection light axis oriented in a direction substantially orthogonal to the vertical direction.

6. The microscope according to claim 3, wherein the third liquid immersion medium has an index of refraction identical to that of the second liquid immersion medium.

7. The microscope according to claim 1, wherein the light-transmitting section of the specimen container has an index of refraction identical to that of the second liquid immersion medium.

8. The microscope according to claim 1, wherein the light-transmitting section of the medium container has an index of refraction identical to that of the second liquid immersion medium.

9. The microscope according to claim 1, wherein the movable stage supports the specimen container so as to be movable in a direction intersecting the detection light axis.

10. The microscope according to claim 1, wherein the image-capturing unit acquires an image of the light self-emitted by the specimen.

11. The microscope according to claim 1, further comprising:

an illumination optical system that irradiates the specimen with light from a direction intersecting the detection light axis, wherein each of the specimen container and the medium container has a light transmitting section that transmits, towards the specimen, the light coming from the illumination optical system.

12. The microscope according to claim 11, wherein:

the medium container has the light transmitting section, which transmits the light coming from the illumination optical system, at a bottom section, and the illumination optical system includes a reflection mirror placed in the medium container, causes the light to enter the medium container via the light transmitting section at the bottom section, and reflects the light at the reflection mirror towards the specimen.

13. The microscope according to claim 11, wherein:

the medium container has the light transmitting section, which transmits the light coming from the illumination optical system, at a side wall section, and the illumination optical system causes the light to enter the medium container via the light transmitting section at the side wall section.

14. The microscope according to claim 11, wherein the illumination optical system includes a lens that is placed in the medium container and that has positive refractive power.

15. The microscope according to claim 14, wherein the lens having positive refractive power is a cylindrical lens having positive refractive power in one direction intersecting an illumination light axis of the illumination optical system.

16. The microscope according to claim 11, further comprising:

a microlens array formed by two-dimensionally arranging a plurality of microlenses in directions intersecting an imaging light axis of the image-capturing unit, wherein the illumination optical system causes the light in a form of a substantially collimated beam to enter the specimen.

17. The microscope according to claim 11, wherein the movable stage supports a plurality of the specimen containers so as to be movable in the medium container about an axis parallel to the detection light axis.

18. The microscope according to claim 11, wherein:

the specimen container has a plurality of specimen accommodation sections arranged in one direction intersecting an illumination light axis of the illumination optical system, and the movable stage supports the specimen container so as to be capable of switching the specimen accommodation section placed on the detection light axis.

19. The microscope according to claim 11, wherein the movable stage supports the specimen container so as to be rotatable in the medium container about the detection light axis.

20. The microscope according to claim 11, wherein the illumination optical system causes the light in a flat shape to enter the specimen along a plane intersecting the detection light axis of the objective lens.

* * * * *